US008843212B2

(12) United States Patent
Lloyd et al.

(10) Patent No.: US 8,843,212 B2
(45) Date of Patent: *Sep. 23, 2014

(54) MRI COMPATIBLE CO-RADIALLY WOUND LEAD ASSEMBLY

(71) Applicant: Imricor Medical Systems, Inc., Burnsville, MN (US)

(72) Inventors: Thomas W. Lloyd, Eagan, MN (US); Steven R. Wedan, Savage, MN (US); Gregg S. Stenzel, Victoria, MN (US)

(73) Assignee: Imricor Medical Systems, Inc., Burnsville, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/063,566

(22) Filed: Oct. 25, 2013

(65) Prior Publication Data

US 2014/0058491 A1 Feb. 27, 2014

Related U.S. Application Data

(60) Continuation of application No. 13/371,035, filed on Feb. 10, 2012, now Pat. No. 8,588,938, which is a division of application No. 12/743,954, filed as application No. PCT/US2010/026232 on Mar. 4, 2010, now Pat. No. 8,588,934.

(60) Provisional application No. 61/157,482, filed on Mar. 4, 2009.

(51) Int. Cl.
| | |
|---|---|
| *A61N 1/05* | (2006.01) |
| *A61N 1/08* | (2006.01) |
| *A61B 5/042* | (2006.01) |
| *A61B 17/00* | (2006.01) |
| *A61B 18/14* | (2006.01) |
| *A61B 5/055* | (2006.01) |

(52) U.S. Cl.
CPC ......... *A61N 1/08* (2013.01); *A61B 2017/00911* (2013.01); *A61B 18/1492* (2013.01); *A61B 5/0422* (2013.01); *A61N 2001/086* (2013.01); *A61B 5/055* (2013.01)

USPC .......................................... 607/116

(58) Field of Classification Search
CPC ............................... A61N 2001/086
USPC .......................................... 607/116
See application file for complete search history.

(56) References Cited

U.S. PATENT DOCUMENTS

| 3,380,004 A | 4/1968 | Hansen |
| 5,039,964 A | 8/1991 | Ikeda et al. |

(Continued)

FOREIGN PATENT DOCUMENTS

WO    WO 2007/047966 A2    4/2007

OTHER PUBLICATIONS

Third Party Submission under 37 C.F.R. 1.290, filed on corresponding U.S. Appl. No. 13/836,287; dated Jan. 22, 2014, 7 pages.

(Continued)

*Primary Examiner* — Joseph Stoklosa
(74) *Attorney, Agent, or Firm* — Barbara A. Wrigley; Oppenheimer Wolff & Donnelly LLP

(57) ABSTRACT

An MRI compatible lead assembly construct is provided. The construct includes at least two filter components constructed from an electrode wire. One filter component may be a resonant LC filter at or near an electrode/wire interface that resolves the issue of insufficient attenuation by effectively blocking the RF induced current on the wire from exiting the wire through the electrode. The second filter component may include one or more non-resonant filter(s) positioned along the length of the electrode wire that resolve(s) the issue of excessive heating of the resonant LC filter by significantly attenuating the current induced on the wire before it reaches the resonant LC filter. The non-resonant filter(s) may also attenuate the RF current reflected from the resonant LC filter thereby resolving the issue of the strong reflected power from the resonant filter and the associated dielectric heating.

21 Claims, 7 Drawing Sheets

(56) References Cited

U.S. PATENT DOCUMENTS

| | | |
|---|---|---|
| 5,209,233 A | 5/1993 | Holland et al. |
| 5,217,010 A | 6/1993 | Tsitlik et al. |
| 5,304,219 A | 4/1994 | Chernoff et al. |
| 5,510,945 A | 4/1996 | Taylor et al. |
| 5,867,891 A | 2/1999 | Lampe |
| 5,951,539 A | 9/1999 | Nita et al. |
| 6,493,590 B1 | 12/2002 | Wessman et al. |
| 7,013,180 B2 | 3/2006 | Villaseca et al. |
| 7,174,219 B2 | 2/2007 | Wahlstrand |
| 7,363,090 B2 | 4/2008 | Halperin et al. |
| 7,689,288 B2 | 3/2010 | Stevenson et al. |
| 7,702,387 B2 | 4/2010 | Stevenson et al. |
| 7,751,903 B2 | 7/2010 | Stevenson et al. |
| 7,844,319 B2 | 11/2010 | Susil et al. |
| 7,844,343 B2 | 11/2010 | Wahlstrand |
| 7,899,551 B2 | 3/2011 | Westlund et al. |
| 7,945,322 B2 | 5/2011 | Stevenson et al. |
| 7,983,764 B2 | 7/2011 | Bodner |
| 8,145,324 B1 | 3/2012 | Stevenson et al. |
| 8,364,283 B2 | 1/2013 | Halperin et al. |
| 8,588,934 B2 | 11/2013 | Lloyd et al. |
| 8,588,938 B2 | 11/2013 | Lloyd et al. |
| 2002/0016589 A1 | 2/2002 | Swartz et al. |
| 2002/0095084 A1 | 7/2002 | Vrijheid et al. |
| 2003/0050557 A1 | 3/2003 | Susil et al. |
| 2003/0130738 A1 | 7/2003 | Hovda et al. |
| 2003/0135101 A1 | 7/2003 | Webler |
| 2003/0144721 A1 | 7/2003 | Villaseca et al. |
| 2004/0199069 A1 | 10/2004 | Connelly et al. |
| 2005/0222659 A1 | 10/2005 | Olsen et al. |
| 2005/0228452 A1 | 10/2005 | Mourlas et al. |
| 2006/0247684 A1 | 11/2006 | Halperin et al. |
| 2007/0018535 A1 | 1/2007 | Guedon et al. |
| 2007/0112398 A1 | 5/2007 | Stevenson et al. |
| 2007/0197890 A1 | 8/2007 | Boock et al. |
| 2007/0288058 A1 | 12/2007 | Halperin et al. |
| 2008/0024912 A1 | 1/2008 | Mallary et al. |
| 2008/0049376 A1 | 2/2008 | Stevenson et al. |
| 2008/0071313 A1 | 3/2008 | Stevenson et al. |
| 2008/0116997 A1 | 5/2008 | Dabney et al. |
| 2008/0119919 A1 | 5/2008 | Atalar et al. |
| 2008/0132985 A1 | 6/2008 | Wedan et al. |
| 2008/0132987 A1 | 6/2008 | Westlund et al. |
| 2008/0186123 A1 | 8/2008 | Wei et al. |
| 2008/0243218 A1 | 10/2008 | Bottomley et al. |
| 2008/0262584 A1 | 10/2008 | Bottomley et al. |
| 2009/0171421 A1 | 7/2009 | Atalar et al. |
| 2009/0243756 A1 | 10/2009 | Stevenson et al. |
| 2010/0016936 A1 | 1/2010 | Stevenson et al. |
| 2010/0100164 A1 | 4/2010 | Johnson et al. |
| 2010/0114276 A1 | 5/2010 | Min et al. |
| 2010/0160997 A1 | 6/2010 | Johnson et al. |
| 2010/0191236 A1 | 7/2010 | Johnson et al. |
| 2011/0046707 A1 | 2/2011 | Lloyd et al. |
| 2012/0071956 A1 | 3/2012 | Stevenson et al. |

OTHER PUBLICATIONS

Extended European Search Report, from corresponding application Serial No. EP 10749339.7, European Patent Office, dated Dec. 5, 2013, 11 pages.

International Search Report and Written Opinion, from corresponding application (PCT/US10/26232), U.S. Receiving Office, dated Apr. 30, 2010, 11 pages.

International Search Report and Written Opinion, from corresponding application (PCT/US13/44685), U.S. Receiving Office, dated Sep. 10, 2013, 10 pages.

Ozenbaugh, Richard Lee, et al., "Network Analysis of Passive LC Structures, " EMI Filter Design, Third Edition: 2011, pp. 18-1 to 18-11. CRC Press.

Whitaker, Jerry C., "Filter Devices and Circuits," The Resource Handbook of Electronics; 2001, 11 pages, CRC Press LLC, USA.

Third-Party Submission Under 37 C.F.R. 1.290, mailed on Apr. 10, 2014, in corresponding U.S. Appl. No. 14/063,665; 9 pages.

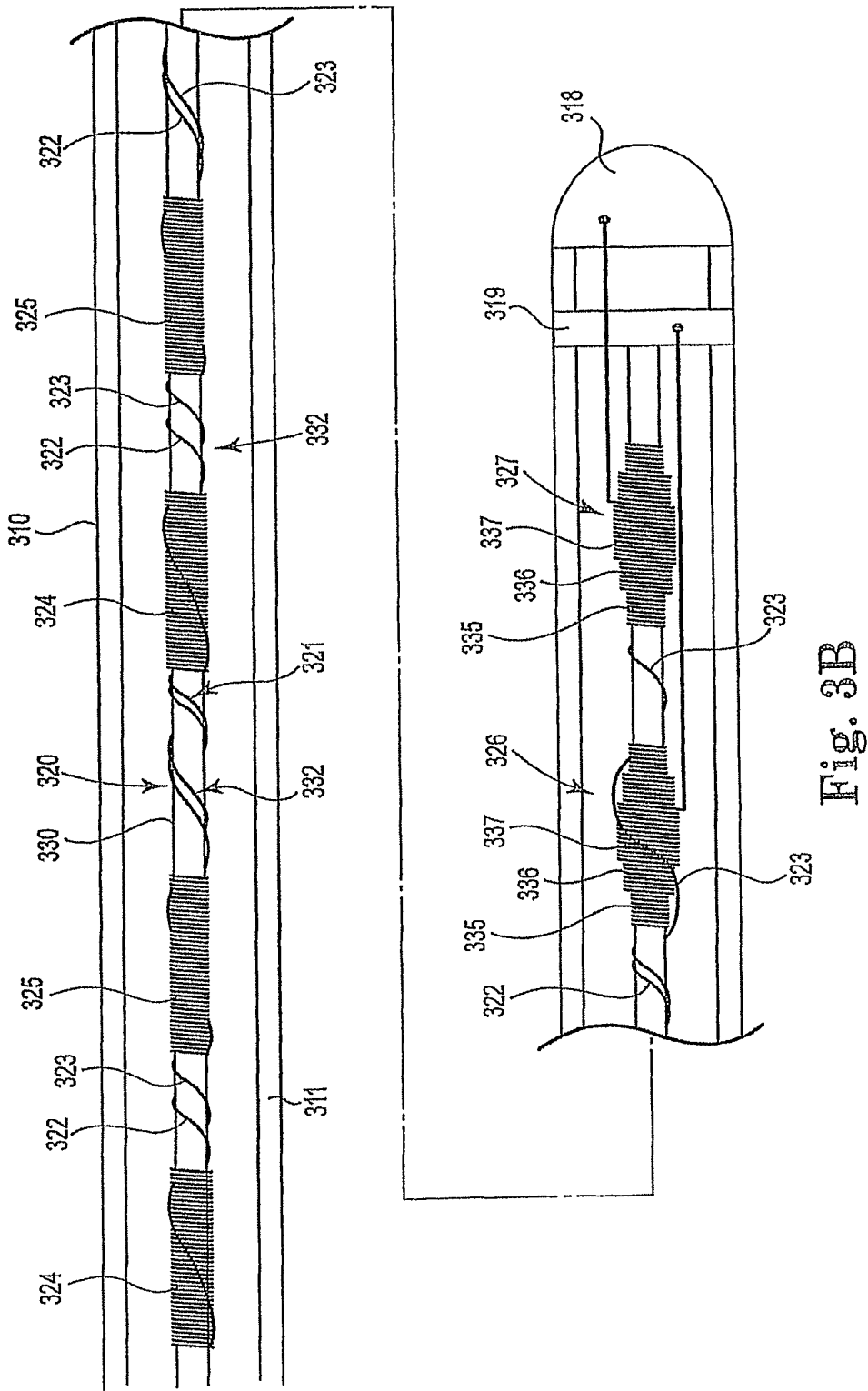

MRI COMPATIBLE CO-RADIALLY WOUND LEAD ASSEMBLY

CROSS-REFERENCED APPLICATIONS

This application is a continuation of U.S. application Ser. No. 13/371,035 filed on Feb. 10, 2012, which claims the benefit of U.S. application Ser. No. 12/743,954, filed on May 20, 2010, which claims the benefit of PCT application Serial No. PCT/US2010/026232, filed on Mar. 4, 2010, which claims the benefit of U.S. provisional application Ser. No. 61/157,482, filed on Mar. 4, 2009, the entireties of which are hereby incorporated by reference.

FIELD OF THE INVENTION

The invention relates to medical devices with tissue contacting electrodes used in the magnetic resonance imaging (MRI) environment and in particular to a method and device for attenuating electromagnetic fields applied to such devices during MRI scanning.

BACKGROUND OF THE INVENTION

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

MRI uses three fields to image patient anatomy: a large static magnetic field, a time-varying magnetic gradient field, and a radiofrequency (RF) electromagnetic field. The static magnetic field and time-varying magnetic gradient field work in concert to establish proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI presents safety risks to patients when a medical device is in close proximity to or in contact either externally or internally with patient tissue. One important safety risk is the heating that can result from an interaction between the RF field of the MRI scanner and the medical device (RF-induced heating), especially medical devices which have elongated conductive structures with tissue contacting electrodes, such as electrode wires in pacemaker and implantable cardioverter defibrillator (ICD) leads, guidewires, and catheters. Thus, as more patients are fitted with implantable medical devices, and as use of MRI diagnostic imaging continues to be prevalent and grow, the need for safe devices in the MRI environment increases.

A variety of MRI techniques are being developed as alternatives to X-ray imaging for guiding interventional procedures. For example, as a medical device is advanced through the patient's body during an interventional procedure, its progress may be tracked so that the device can be delivered properly to a target site. Once delivered to the target site, the device and patient tissue can be monitored to improve therapy delivery. Thus, tracking the position of medical devices is useful in interventional procedures. Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the position of medical devices using MRI is also useful in oncological procedures such as breast, liver and prostate tumor ablations; and urological procedures such as uterine fibroid and enlarged prostate ablations.

The RF-induced heating safety risk associated with electrode wires in the MRI environment results from a coupling between the RF field and the electrode wire. In this case several heating related conditions exist. One condition exists because the electrode wire electrically contacts tissue through the electrode. RF currents induced in the electrode wire may be delivered through the electrode into the tissue, resulting in a high current density in the tissue and associated Joule or Ohmic tissue heating. Also, RF induced currents in the electrode wire may result in increased local specific absorption of RF energy in nearby tissue, thus increasing the tissue's temperature. The foregoing phenomenon is referred to as dielectric heating. Dielectric heating may occur even if the electrode wire does not electrically contact tissue, such as if the electrode was insulated from tissue or if no electrode was present. In addition, RF induced currents in the electrode wire may cause Ohmic heating in the electrode wire, itself, and the resultant heat may transfer to the patient. In such cases, it is important to attempt to both reduce the RF induced current present in the electrode wire and to limit the current delivered into the surrounding tissue.

Methods and devices for attempting to solve the foregoing problem are known. For example, high impedance electrode wires limit the flow of current and reduce RF induced current; a resonant LC filter placed at the wire/electrode interface may reduce the current delivered into the body through the electrodes, non-resonant components placed at the wire/electrode interface may also reduce the current transmitted into the body; and co-radial electrodes wires may be used to provide a distributed reactance along the length of the wire thus increasing the impedance of the wire and reducing the amount of induced current.

Notwithstanding the foregoing attempts to reduce RF-induced heating, significant issues remain. For example, high impedance electrode wires limit the functionality of the electrode wire and do not allow for effective ablation, pacing or sensing. Resonant LC filters placed at the wire/electrode interface inherently result in large current intensities within the resonant components resulting in heating of the filter itself, at times exceeding 200.degree. C. Additionally, a resonant LC filter at the wire/electrode interface can result in a strong reflection of the current induced on the electrode wire and may result in a standing wave that increases the temperature rise of the wire itself and/or results in increased dielectric heating near the electrode wire which in turn heats surrounding tissue to potentially unacceptable levels and may melt the catheter or lead body in which it is housed. Non-resonant components alone do not provide sufficient attenuation to reduce the induced current to safe levels. Additionally, the components will experience a temperature rise, if the conductor cross-sectional area is too small. While an electrode wire with distributed reactance (i.e. coiled wires) can reduce the level of induced current on the wire, it does not sufficiently block the current that is induced on the wire from exiting the wire through the electrodes. Thus, while coiled wires may work for certain short lengths or distances, in situations requiring longer lengths or distances, coiled wires do not by themselves provide enough impedance to block current.

Current technologies for reducing RF-induced heating in medical devices, especially those with elongated conductive structures such as electrode wires, are inadequate. Therefore, new electrode wire constructs and lead or catheter assemblies are necessary to overcome the problems of insufficient attenuation of RF energy.

BRIEF SUMMARY OF THE INVENTION

It is an object of the invention to provide an improved device and method for reducing RF-induced heating of tissue by attenuating the RF current induced in the medical device by MRI.

It is a further object of the invention to provide a novel circuit construction that is MRI compatible and resolves the limitations of the current technology such as insufficient attenuation of RF energy.

It is a further object of the invention to provide a novel circuit construction that maintains physical flexibility, maneuverability and the ability to bend.

In one embodiment the invention is a circuit adapted to be used with an implantable or interventional lead or catheter assembly. Each circuit includes a plurality of filter components constructed from a single wire.

In one embodiment the filter component comprises two filter components. One filter component may be a resonant filter at or near the electrode/wire interface that resolves the issue of insufficient attenuation by effectively blocking the RF induced current on the wire from exiting the wire through the electrode. The second filter component may comprise one or more non-resonant filter(s) or inductors positioned along the length of the wire that resolve(s) the issue of excessive heating of the resonant LC filter by significantly attenuating the current induced on the wire before it reaches the resonant LC filter. The non-resonant filters(s) may also attenuate the RF current reflected from the resonant LC filter thereby resolving the issue of the strong reflected power from the resonant filter and the associated dielectric heating.

In one embodiment, the non-resonant filters may comprise a plurality of multiple inductors placed in close proximity such as within approximately 1 cm or less for the purpose of providing more attenuation than a single filter alone, while still allowing the device to bend.

In one embodiment, multiple non-resonant filters placed in close proximity may be formed to create a distributed reactance. For example, two co-radially wound electrode wires may create a distributed reactance. In an alternative embodiment three or more co-radially wound electrode wires may include create a distributed reactance. A further alternative embodiment may include the use of two or more coaxially wound wires for the electrodes.

In one embodiment, the novel lead assembly construct may include a single wire thereby eliminating the need for bonding points which reduces the possibility of mechanical failure of the wire.

In one embodiment an electrode wire has a cross sectional area such that the resistivity of the wire at the MR operating frequency, 64 MHz for a 1.5 T MRI for example, is low enough to ensure that heating of the wire is minimal.

In one embodiment the lead assembly and integrated components may be constructed to be integrated into a 10 French or smaller catheter.

In one embodiment the lead assembly may be used in an implanted medical device such as ICDs, pacemakers, neurostimulators, and the like.

In one embodiment a catheter or lead assembly includes an elongated body having first and second ends. The elongate body defines a lumen therewithin which receives first and second circuits. First and second circuits each include an electrode wire that forms a plurality of filters distributed along a length thereof. A tip electrode located at the distal end of the elongate body is coupled to the second electrode wire. The elongate body also includes a ring electrode at the first end and proximal to the tip electrode. The ring electrode is electrically coupled to the first wire. The second end of the elongate body is operably coupled to electronic controls, either external or internal to the body. In one embodiment, the second end attaches to amplifiers for sensing cardiac activity, as well as a pacing circuit to stimulate cardiac tissue. The second end may also be connected to an RF ablation generator to ablate, for example, cardiac tissue. One filter formed by each electrode wire may be a resonant LC filter at or near the electrode/wire interface that resolves the issue of insufficient attenuation by effectively blocking the RF induced current on the wire from exiting the wire through the electrode. A second filter formed by each electrode wire may comprise one or more non-resonant filter(s) or inductors positioned along the length of the elongate body that resolve(s) the issue of excessive heating of the resonant LC filter by attenuating the current induced on the wire before it reaches the resonant LC filter. The non-resonant filter(s) may also attenuate the RF current reflected from the resonant LC filter thereby resolving the issue of the strong reflected power from the resonant filter and the associated dielectric heating.

In another embodiment a lead assembly includes an elongated body having first and second ends. A plurality of electrodes is located at the distal end of the elongate body. The plurality of electrodes may include a tip electrode and any number of ring electrodes or may comprise a plurality of ring electrodes. The elongate body further defines a lumen therewithin which receives a plurality of circuits. Each individual electrode wire comprising the plurality of circuits forms a plurality of non-resonant filters, or inductors, distributed along a length thereof. The second end of the elongate body may be operably coupled to electronic controls, either external or internal to the body, amplifiers for sensing cardiac activity, a RF ablation generator, and/or the like. Each individual circuit comprising the plurality of electrode wires also forms a resonant LC filter positioned within the lumen of the elongate body at a distal end thereof at or near the electrode/wire interface.

In another embodiment a lead assembly includes an elongate body having a proximal end and a distal end, the elongate body defining a lumen therewithin. The distal end is arranged and configured to contact tissue and the proximal end is operably coupled to an electronic control. At least one electrode is located on the elongate body and at least one electrical circuit is in communication with the at least one electrode. The circuit is housed within the elongate body and includes one or more electrode wires that form at least one non-resonant filter and at least one resonant LC filter. The resonant LC filter is positioned at the distal end of the elongate body proximate an electrode/wire interface. The circuit may be flexible or rigid.

While multiple embodiments, objects, feature and advantages are disclosed, still other embodiments of the invention will become apparent to those skilled in the art from the

BRIEF DESCRIPTION OF THE DRAWINGS

FIG. 3B shows a detailed view of the resonant LC filters and non-resonant filters of FIG. 3A.

DETAILED DESCRIPTION OF THE INVENTION

In describing the invention herein, reference is made to an exemplary lead assembly comprising a catheter. However, as will be appreciated by those skilled in the art the present invention may be used with any implantable medical device. By implantable we mean permanently as with cardiac pacemakers, defibrillators and neurostimulators; or temporarily implantable such as in interventional procedures and including by way of example cardiac ablation devices and the like. Further the exemplary lead assembly may be used external to the body but still be in contact with body tissue such as the skin. Also as used herein, an electrode wire is any conductive structure that is in electrical contact with an electrode. Typically, an electrode wire is an actual wire; however, an electrode wire may also be a circuit board trace, a conductive lumen, or any material which conducts electricity.

Figure 1:
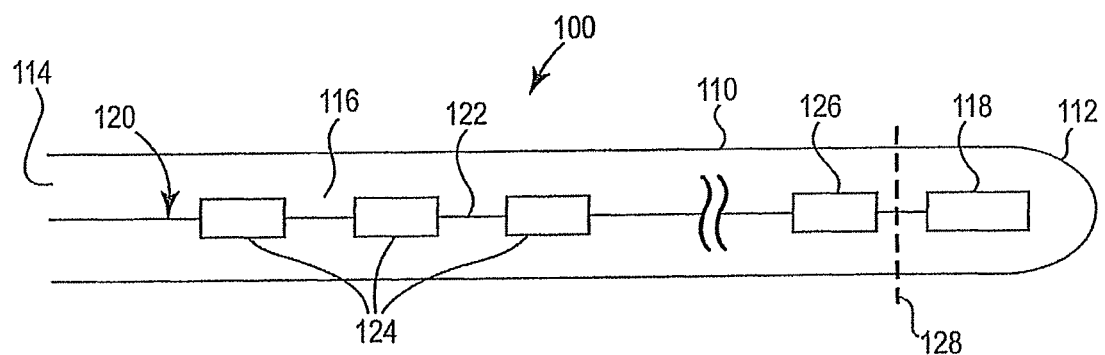
FIG. 1 is a block diagram depicting the basic components of the invention housed within a catheter or lead assembly.

FIG. 1 is a block diagram illustrating the lead assembly 100 in its simplest form in accordance with the present invention. Lead assembly 100 broadly includes elongate body 110 having first 112 and second 114 ends and defining a lumen 116 therewithin. Electrode 118 is located at the first end 112 of elongate body 110 and is in electrical communication with circuit 120. Lumen 116 houses circuit 120. Circuit 120 includes at least one electrode wire 122 forming a plurality of spaced apart filter components 124. Each circuit 120 may be constructed from a single, continuous length of wire. Alternatively, the circuit 120 may be constructed with discrete filter components and a single electrode wire or multiple lengths of non-continuous electrode wire connecting the discrete filter components. Alternatively, the circuit 120 may be constructed with one electrode wire forming filter components 124 and a discrete electrode wire forming filter component 126. Any non-magnetic wire may be used in constructing the circuit in accordance with the present invention, including copper, titanium, titanium alloys, tungsten, gold and combinations of the foregoing. Optionally, electrode wire 120 is a bondable wire such as heat, chemical or adhesively bondable to permit formation of the filters during manufacture with one wire. In the case in which multiple lengths of wire are used as connecting segments, the wires may be cast in silicone and/or heat-treated along the length at certain points to ensure that the wire does not shift. Alternatively, any wire that is sufficiently rigid so that it holds its shape when bent may be used. Electrode wire 120 may also form filter component 126 positioned adjacent the wire/electrode interface 128 to effectively block RF induced current from exiting the lead assembly through the electrode 118. Additional filtering components 124 distributed along the length of the wire attenuate the induced current on the wire itself before the current reaches filter component 126 thereby avoiding excessive heating of filter component 126. Excessive heating will occur when the temperature of the filter rises approximately 2 to 4 degrees above the normal temperature of the tissue that the device contacts.

Preferably, filter component 126 at the electrode/wire interface 128 is a resonant LC filter that resolves the problem of insufficient attenuation by effectively blocking the RF induced current on wire 122. Filter components 124 preferably include a plurality of non-resonant filters or inductors that address excessive heating of the resonant LC filter by significantly attenuating the current induced on the wire before the current reaches the resonant LC filter. Non-resonant filter components 124 may also attenuate the RF current reflected from resonant LC filter component 126 thereby attenuating the strong reflected power from the resonant LC filter 126 and reducing the associated dielectric heating.

Figure 2:
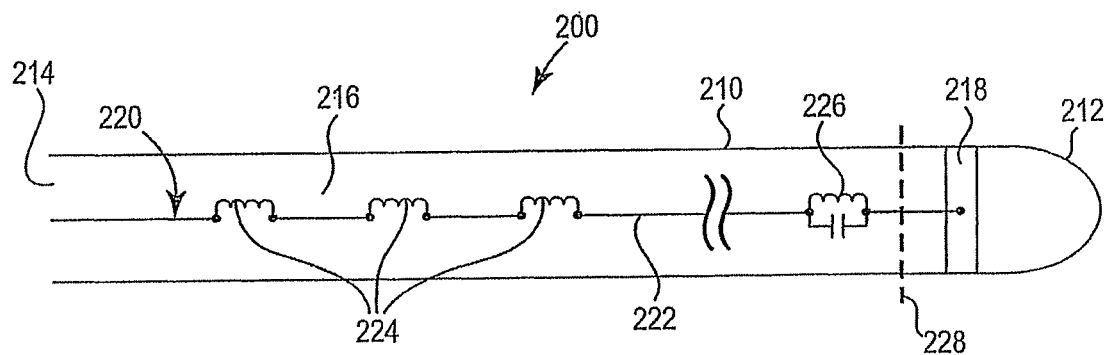
FIG. 2 is a diagram depicting an embodiment of the invention in which non-resonant filters are distributed along a wire in a spaced apart relationship with a resonant LC filter proximate an electrode.

FIG. 2 is a schematic diagram depicting an embodiment of the invention. Lead assembly 200 broadly includes an elongate body 210 having first 212 and second 214 ends and includes lumen 216 therewithin. Lead or catheter assembly 200 includes first electrode 218 located at the first end 212 of lead assembly 200. First electrode 218 may be a tip electrode. Alternatively, first electrode may be a ring electrode or other electrodes known to those skilled in the art. Lumen 216 houses circuit 220. Circuit 220 includes at least one conductive electrode wire 222 forming a plurality of spaced apart filter components 224. Each circuit may constructed from a single, continuous length of non-magnetic wire such as copper, titanium, titanium alloys, tungsten, gold and combinations of the foregoing. Alternatively, each circuit may comprise multiple lengths of wires. As with the embodiment depicted in FIG. 1, electrode wire 222 is a bondable wire such as heat, chemical or adhesively bondable to permit formation of the filters during manufacture with one wire. This eliminates the necessity for connection points at each end of each filter 224 and thereby improving the mechanical durability of the circuit 220 and reducing the manufacturing cost thereof. In the illustrated embodiment, the lead assembly 200 includes resonant LC filter 226 positioned adjacent and proximal to the wire/electrode interface 228. Resonant LC filter assembly 226 is adapted to effectively block RF induced current from exiting the lead assembly 200 through the electrode 218. Resonant LC filter 226 effectively blocks RF induced current by being constructed such that the inductive and capacitive characteristics of the filter together resonate to create a high impedance at the MRI RF frequency of interest for example, approximately 64 MHz for a 1.5 Tesla MRI or approximately 128 MHz for a 3.0 Tesla MRI. Filtering components 224 distributed along the length of the wire attenuate the induced current on the wire itself before the current reaches resonant LC filter 226 thereby avoiding excessive heating of resonant LC filter 226. The filtering components 224 together preferentially create at least 1,000 or more Ohms of impedance along the entire circuit 220, for a lead length of approximately 1 meter. Those of skill in the art will appreciate that the amount of total impedance will necessarily change as the lead length varies. Each filtering component 224 may comprise an inductor formed by electrode wire 222 with approximately 45 turns, creating approximately 150 Ohms, when sized to fit in an 8 French catheter assuming an inside diameter of the inductor to be 0.045 inches. Fewer turns are necessary to create the same impedance for larger diameter inductors. Filtering components 224 may be spaced non-uniformly, such that the segments of wire between them each have a different resonant frequency, or substantially uniformly.

Figure 3A:
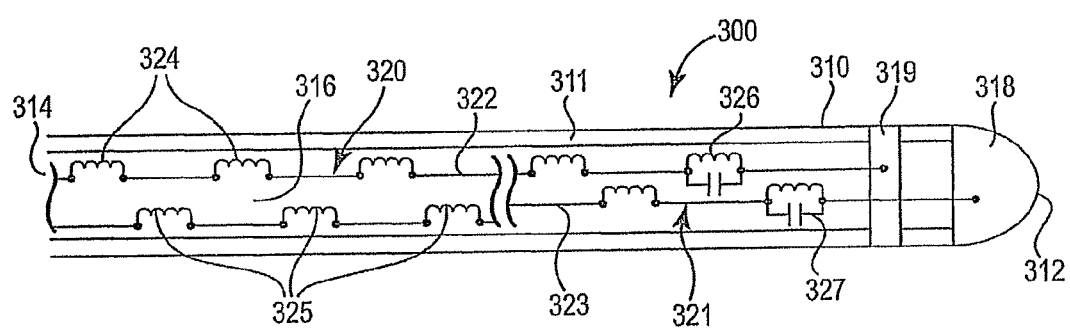
FIG. 3A is a sectional view of an exemplary medical device including MR compatible conductive electrode wires forming non-resonant filters distributed along the wire and each wire forming a resonant LC filter proximate an electrode.

Referring now to FIG. 3A a detailed sectional view of one embodiment of the invention is illustrated. Lead assembly 300 includes elongate body 310 surrounded by jacket 311. Elongate body 310 includes first 312 and second 314 ends and includes lumen 316 therewithin. Second end 314 is adapted to be connected to electronic controls, internal or external to the patient body, and may include a connector (not shown). Lumen 316 houses circuits 320, 321. Circuits 320, 321 each include one conductive electrode wire 322, 323, respectively, located within the lumen 316 of lead assembly 300. In an alternative embodiment, conductive electrode wires 322, 323 can be embedded in jacket 311, as seen in FIG. 4B, thereby decreasing the overall diameter of the lead assembly 300. Each conductive electrode wire 322, 323 comprises a single length of conductive wire, each of which forms a plurality of spaced apart filter components 324, 325, respectively. Filter components 324, 325 comprise non-resonant filters or inductors that are spaced apart along the length of conductive electrode wires 322, 323. Electrodes 319, 318 are located on the first end 312 of elongate body 310 and are electrically coupled to the first and second conductive wires 322, 323, respectively. In the illustrated embodiment, first electrode 319 is a ring electrode and second electrode 318 is a tip electrode. However, the electrodes 318, 319 may be any type of electrodes known to those skilled in the art of lead assemblies. For example, the electrode may be a single tip electrode. Alternatively, the electrodes may be one or a series of ring electrodes. Still yet alternatively, the electrodes may be electrodes placed on either side of the housing. Thus although the illustrated embodiment is depicted as including tip and ring electrodes any of the foregoing electrodes fall within the scope of the invention.

The first and second conductive wires 322, 323 are electrically insulated from one another. Both the first and second conductive wires 322, 323 may include an insulative or non-conductive coating. Preferably the insulative coating is a heat bondable material such as polyurethane, nylon, polyester, polyester-amide, polyester-imide, polyester-amide-imide and combinations of the foregoing. Alternatively, only one wire may be insulated. The wire insulation comprises the bondable material mentioned previously. In addition, circuits 320, 321, as best seen in FIG. 3B, are further electrically insulated as both electrode wires 322, 323 are wound around non-conductive tube 330 defining a lumen therewithin. Tube 330 may be formed of a silicone material, Teflon, expanded tetrafluoroethylene (eTFE), polytetrafluoroethylene (pTFE), or the like, as described below. Winding the non-resonant filters 324, 325 or inductors around non-conductive tube 330 facilitates construction of the inductors and resonant LC circuit. Moreover, non-conductive tube 330 advantageously allows the circuits to maintain flexibility and maneuverability when placed inside an elongate body. Advantageously, other items necessary or desirably used in the surgical or interventional procedure such as fiber optic cables, irrigation lumens, coaxial cables may also be passed through the lumen of tube 330.

Referring to FIG. 3A, ring electrode 319 is coupled to the first conductive wire 322 with tip electrode 318 located distal to the ring electrode 319 and coupled to the second conductive wire 323 at the first end 312 of lead assembly 300. Lumen 316 houses circuits 320, 321 comprising electrode wires 322, 323, respectively. Alternatively, and as best illustrated in FIG. 4B, electrode wires 322, 323 may be embedded wholly or partially in jacket 311. As discussed previously, each electrode wire 322, 323 forms a plurality of spaced apart filter components 324, 325 comprising non-resonant filters. As in previous embodiments, each circuit is optionally constructed from a single, continuous length of non-magnetic wire such as copper, titanium, titanium alloys, tungsten, gold and combinations of the foregoing; however, each circuit may alternatively be constructed from multiple lengths of electrode or include discrete filter components connected by separate lengths of electrode wires. If all filters are formed from one length of wire, it is important that the wire is a bondable wire such as heat, chemical or adhesively bondable to permit formation of the filters during manufacture with one wire as will be described below.

Referring now to FIG. 3B each circuit 320, 321 is constructed substantially similarly. Electrode wires 322, 323 are wound over flexible tube 330 which is preferably made from polyimide, polyolefin, pTFE, eTFE, polyetherketone (PEEK) and other similar flexible materials. During manufacture a stiff rod (not shown) is placed inside of flexible tube 330 to provide added support for the assembly process. After manufacture, the rod is removed and the flexible tubing 330 with circuit constructs is placed in elongate body 310.

Each circuit 320, 321 is constructed separately with the first circuit 320 being constructed from the distal end to the proximal end starting with the most proximal resonant LC filter 326. Thus, assuming a plurality of circuits, the electrode wire associated with the next most distal resonant LC filter 327 passes over the resonant LC filter that is most proximal. Passing an electrode wire below a resonant LC filter will adversely affect its resonance. On the other hand, passing a wire underneath a non-resonant inductor will not adversely affect its performance. Thus, exemplary resonant LC filter 326 is constructed by layering of the electrode wire 322 to form three layers 335, 336, 337. The ratio of turns from inner layer to outer layer may be approximately 3:2:1 resulting in a constant physical geometry of the resonant LC filter. Creating a resonant LC filter is apparent to those skilled in the art, and many embodiments would satisfy the requirements of this invention. For example, a capacitor may be placed in parallel with an inductor. Other types of resonant LC filters would also fall within the scope of the invention.

In the exemplary embodiment, multiple layers of coiled wire are constructed such that the capacitance between the layers and individual turns provide the ratio of inductance to capacitance required to satisfy the resonant condition and provide the maximum impedance at the resonant frequency. As described previously, three layers may be used, the ratio of turns from inner layer to outer layer being approximately 3:2:1. This ratio results in high structural integrity, manufacturability, and repeatability. In the exemplary embodiment, wherein the resonant frequency of the resonant LC filter is approximately 64 MHz to block the RF from a 1.5 Tesla MRI, the inner layer may include 30 turns, the middle layer may include 20 turns, and the outer layer may include 10 turns. In general, the exact number of turns is determined by the space available and the desired resonant frequency. The impedance, bandwidth and quality factor of the resonant LC filter can be adjusted by modifying the ratio of the capacitance to the inductance of the filter. This may be accomplished by changing the number of turns, the number of layers, the ratio of turns between layers, or all of these. For example, the ratio may vary in each case by one, two or three turns to obtain the desired characteristics of the filter.

After forming the most proximal resonant LC filter 326, first electrode wire 322 is helically wound around tube 330. Those of skill in the art will appreciate that connecting segments 332 do not necessarily need to comprise a specific numbers of turns around tube 330. Rather, it is important to wind the electrode wires in such a manner as to include some slack or "play" thereby allowing the lead assembly to maintain its flexibility during use. Inductors 324 are next formed by coiling electrode wire 322 over flexible tube 330. Each inductor 324 may be formed by helically winding or coiling electrode wire 322 approximately forty-five turns, creating approximately 150 ohms, when sized to fit in an 8 French catheter assuming an inside diameter of the inductor to be 0.045 inches. Those of skill in the art will appreciate, however, that fewer turns may be necessary to create the same impedance for larger diameter inductors. Inductors 324 may be spaced non-uniformly, such that the segments of wire between them each have a different resonant frequency, or may be placed substantially uniformly.

Second circuit 321 is constructed next and substantially similarly to circuit 320. Those of skill in the art will appreciate that the exemplary lead assembly illustrated in FIGS. 3A and 3B comprises two circuits 320, 321 and two electrodes 319 and 318. However, any number of circuits and corresponding electrodes can be constructed. For example, in one exemplary construct four circuits each comprising a plurality of non-resonant filters and a resonant LC filter are electrically coupled to four electrodes (three ring electrodes and one tip electrode or alternatively four ring electrodes). In another exemplary construct ten circuits each comprising a plurality of non-resonant filters and a resonant LC filter are electrically coupled to ten electrodes. Any number of circuits can be constructed. In each case, however, the circuit that includes the most proximal resonant LC filter is constructed first and the circuit that includes the most distal resonant LC filter is constructed last so that the plurality of resulting electrode wires housed within a catheter have the connecting electrode wire segments passing over all proximal resonant LC filters. For example, constructing circuits 320, 321 may be done by starting at the proximal end first (rather than the distal end) so long as the circuit that includes the most proximal resonant LC filter is constructed first. In this way the connecting electrode wire segments of the subsequently constructed circuits will always pass over all adjacent, proximal resonant LC filters so that resonance is not disturbed. Other assembly techniques will be apparent to those of skill in the art.

Figure 4A:
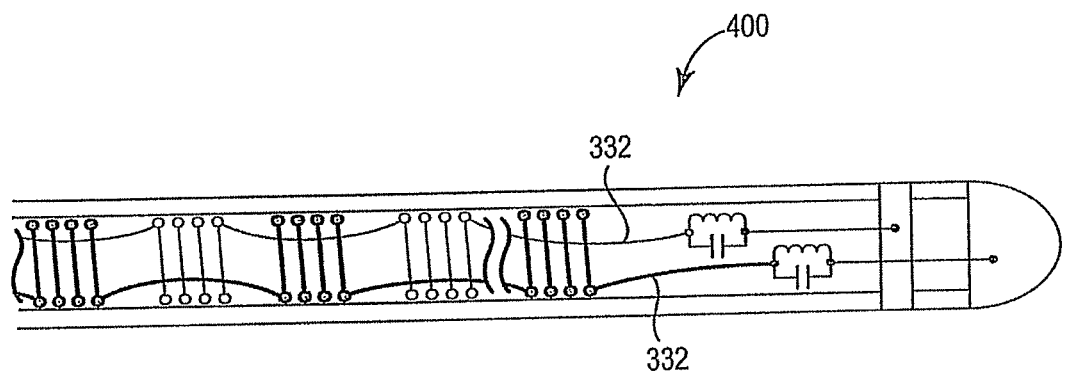
FIG. 4A is a schematic view of the exemplary medical device of FIG. 3 with MR compatible electrode wires positioned within the lumen of the lead assembly.
Figure 4B:
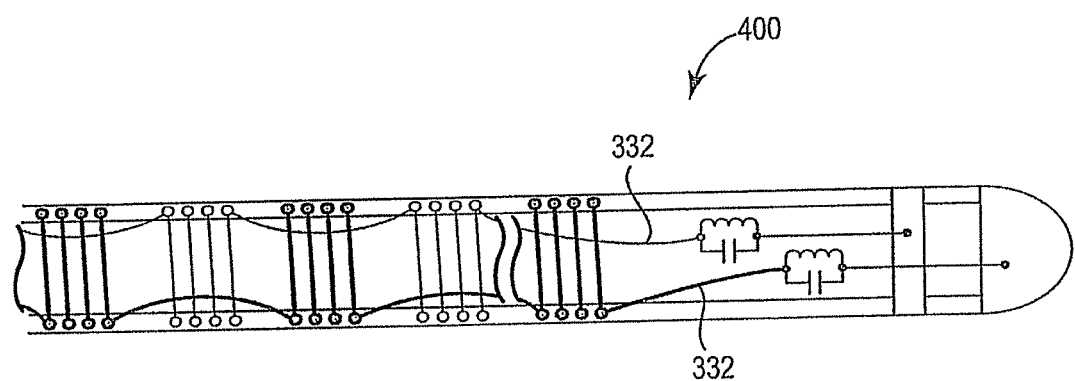
FIG. 4B is a schematic view of an exemplary medical device with MR compatible electrode wires embedded in a jacket surrounding the lead assembly.

As shown in FIGS. 4A and 4B the circuits can be constructed so that the resonant and/or non-resonant filters may be embedded, partially or wholly, in the catheter jacket.

Figure 5:
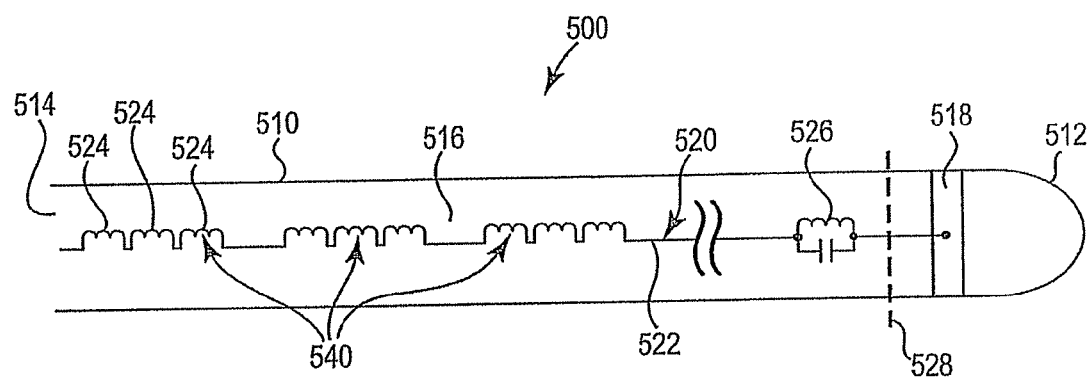
FIG. 5 depicts an embodiment of the invention in which multiple non-resonant inductors formed from a single wire are grouped together and distributed along the wire and further forming a resonant LC filter proximate an electrode.

Referring now to FIG. 5 one embodiment of the invention is shown. In this exemplary circuit 520, multiple, small non-resonant filters 524 are grouped together to form a plurality of inductors 540 positioned in a spaced apart relationship along the length of conductive electrode wire 522. This grouping of filters collectively increases the impedance of each non-resonant filter and reduces the current along the conductive electrode wire 522. As in other embodiments filter component at the electrode/wire interface 528 includes resonant LC filter 526 that is adapted to effectively block RF induced current from exiting the lead assembly 500 through electrode 518. Groups 540 of non-resonant filters 524 distributed along the length of electrode wire 522 attenuate the induced current on the wire itself before the current reaches resonant LC filter 526 thereby avoiding excessive heating of resonant LC filter 526. Groups 540 of non-resonant filters 524 may also attenuate the RF current reflected from resonant LC filter 526 thereby attenuating the strong reflected power from the resonant LC filter 526. The embodiment depicted in FIG. 5 is constructed in much the same way as previously described with respect to FIG. 3B.

Figure 6A:
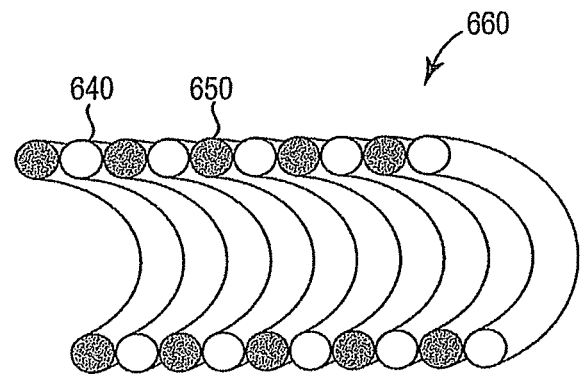
FIG. 6A is a perspective view depicting co-radially wound electrode wires.
Figure 6B:
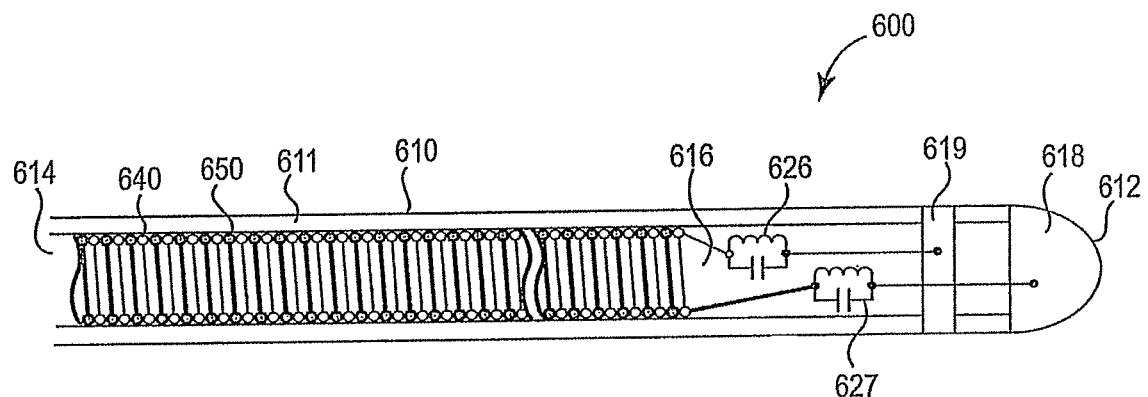
FIG. 6B is a schematic view of the co-radially wound wires of FIG. 6A positioned inside an exemplary medical device with resonant LC filters proximate electrodes.
Figure 6C:
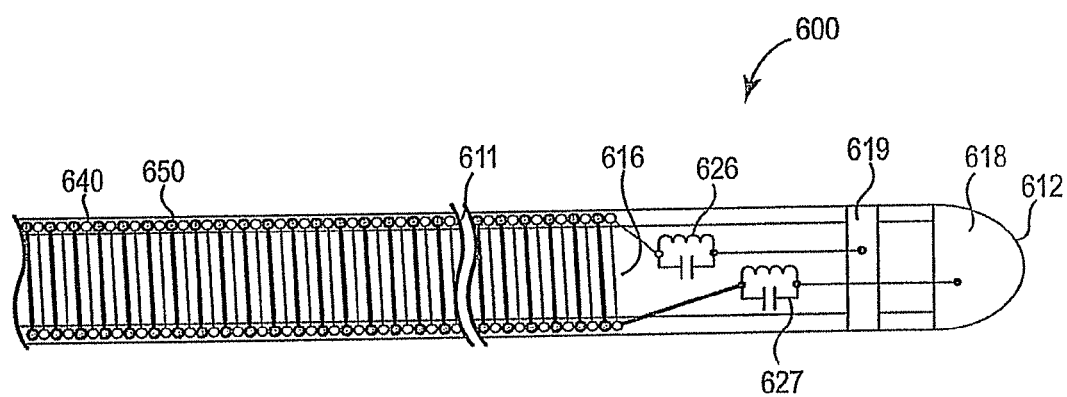
FIG. 6C is a schematic view of the co-radially wound wires of FIG. 6A embedded in the jacket of the exemplary medical device with resonant LC filters proximate electrodes.

Referring now to FIG. 6A-FIG. 6C an alternative embodiment 600 of the invention is shown. As can be seen in FIG. 6A two electrode wires 640, 650 are provided and wound in a co-radial fashion. The co-radially wound electrode wires 640, 650 share a common magnetic flux channel in the center of the windings, such that common mode RF present on both wires will tend to cancel and thus be attenuated. This co-radial approach may be expanded to more than two electrode wires and may comprise any number of co-radially wound wires. Those of skill in the art will appreciate that co-radially wound electrode wires behave as non-resonant filters.

Referring to FIG. 6B, lead assembly 600 includes elongate body 610 surrounded by jacket 611. Elongate body 610 includes first 612 and second 614 ends and includes lumen 616 therewithin. Second end 614 is adapted to be connected to electronics, internal or external to the patient body, and may include a connector (not shown). Lumen 616 houses co-radially wound conductive electrode wires 640, 650. In an alternative embodiment, best shown in FIG. 6C, co-radially wound wires 640, 650 may be embedded in jacket 611. Each co-radially wound electrode wire 640, 650 comprises a single length of conductive wire thereby eliminating the need for bonding points and reducing the possibility of mechanical failure of the wire. The conductive electrode wires 640, 650 are wound in the same direction and the coils have the same diameter. When the lead assembly is exposed to an RF field, as during an MRI scan, the co-radially wound electrode wires 640, 650 tend to block higher frequency common mode RF current from being transmitted along the length of an individual conductive wire. Each co-radially wound conductive electrode wire 640, 650 may have an equal or unequal number of turns. Preferably, however, the conductive electrode wires 640, 650 include an equal number of turns to minimize the amount of RF leakage from the coil, such leakage resulting in less effective RF current blocking. In the embodiment shown in FIGS. 6B and 6C, the co-radially wound wires 640, 650 extend substantially along the entire length of the lead assembly, proximal to the resonant LC filter assembly. In other embodiments (not shown) the co-radial conductive electrode wires may extend only along a portion of the lead body.

In the exemplary coiled configuration, first and second conductive wires are electrically insulated from one another. Both the first and second conductive wires 640, 650 may include an insulative or non-conductive coating. The insulative coating may be formed of a polyurethane material, nylon, polyester, polyester-amide, polyester-imide, polyester-amide-imide, silicone material, Teflon, expanded tetrafluoroethylene (eTFE), Polytetrafluoroethylene (pTFE), and the like. Alternatively, only one wire may be insulated. In any case, electrode wires should be electrically isolated from each other.

As in previous embodiments, each co-radially wound electrode wire 640, 650 is constructed from a single, continuous length of non-magnetic wire such as copper, titanium, titanium alloys, tungsten, gold and combinations of the foregoing. If each wire electrode is constructed from one length of wire, it may be a bondable wire such as heat, chemical or adhesively bondable to permit formation of the filters during manufacture with one wire. Alternatively, several lengths of non-continuous wire may be used and still fall within the intended scope of the invention. In such case the wires may be cast in silicone and heat-treated in certain location to ensure that the wire does not shift. Alternatively, glue or a wire having sufficient rigidity so that it holds its shape when bent may be used to prevent the wire comprising the circuit from shifting.

As best seen in FIG. 6B first and second resonant LC filter assemblies 626, 627 are constructed as hereinbefore described. Resonant LC filters 626, 627 may be placed adjacent and proximal to the wire/electrode interface to effectively block RF induced current from exiting the lead assembly through the electrode. Co-radially wound wires 640, 650 act like non-resonant filters and attenuate the induced current on the wire itself before the current reaches the resonant LC filter thereby avoiding excessive heating.

As with other embodiments, electrode wires 640, 650 are co-radially wound over a length of flexible tubing 340 made from polyimide, polyolefin, pTFE, eTFE, polyetherketone (PEK) and other similar flexible materials. The choice between utilizing co-radially wound electrode wires versus discrete inductors on each electrode wire depends on several factors. Co-radially wound wires can be implemented in a smaller diameter lead, since one electrode wire never needs to pass over or under another, except at the resonant LC filters. However, the impedance of the discrete inductor approach may be more predictable and is not as dependent on length or bend of the device.

In the various embodiments presented herein the conductor includes a sufficient cross-sectional area such that the resistivity of the conductor at the MR operating frequency of 64 MHz for a 1.5 Tesla MRI is low enough to ensure that at Joule heating of the wire is minimal. In one embodiment, the wire may be a 36 AWG copper magnet wire for a circuit that is approximately one meter in length. Numerical modeling such as for example Finite Difference Time Domain (FDTD) or Method of Moments may be used to approximate the expected current for a particular device. The length of wire being used and the expected trajectory in the patient determines the desired total impedance across the circuit. Thus, for any particular length of wire the appropriate gauge may then be selected.

A current of 100 mA DC will result in approximately a 10.degree. rise in temperature in a short section of coiled 40 AWG wire. For a 36 AWG wire, the temperature rise is reduced to a 2.degree. rise in temperature. For AC, the conductor resistance increases with frequency. An increase of five fold or greater is possible when comparing the DC resistance to the resistance of 60 MHZ, which directly translates to a greater temperature rise of the conductor for the same power input. The novel electrode wire construct in accordance with the present invention is configured to be integrated into a 10 French or smaller lead assembly or catheter.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A lead assembly comprising:
    an elongate body having a proximal end and a distal end, said elongate body defining a lumen therewithin, the distal end arranged and configured to contact tissue and the proximal end operably coupled to an electronic control;
    at least a first electrode and at least a second electrode located on the elongate body;
    at least a first length of electrode wire and at least a second length of electrode wire co-radially wound within said elongate body;
    a first resonant LC filter formed from said at least a first length of electrode wire, said first resonant LC filter stacked physically in a plurality of layers and a second resonant LC filter formed from said at least a second length of electrode wire, said second resonant LC filter stacked physically in a plurality of layers, said at least a first length of electrode wire in electrical communication with said first electrode and said at least a second length of electrode wire in electrical communication with said second electrode, said first resonant LC filter positioned proximate said first electrode and said second resonant LC filter positioned proximate said second electrode,
    wherein said co-radially wound first and second electrode wires form a non-resonant filter having a substantially uniformly distributed inductance along the length of said non-resonant filter.

2. The lead assembly of claim 1 further comprising at least a third length of electrode wire co-radially wound with said at least a first and at least a second length of electrode wire, said third co-radially wound electrode wire in communication with a third electrode and forming a third resonant LC filter proximate said third electrode.

3. The lead assembly of claim 1 wherein said co-radially wound electrode wires share a common magnetic flux channel in the center of the windings.

4. The lead assembly of claim 3 wherein a common mode RF present on each of said co-radially wound wires cancels and is attenuated.

5. The lead assembly of claim 1 further including a jacket surrounding said elongate body in which said co-radially wound wires are embedded.

6. The lead assembly of claim 1 wherein the co-radially wound electrode wires are wound in the same direction.

7. The lead assembly of claim 1 wherein the resonant LC filters block high frequency common mode RF current in an MR environment.

8. The lead assembly of claim 1 wherein the co-radially wound electrode wires include an equal number of turns.

9. The lead assembly of claim 1 wherein the co-radially wound electrode wires extend along substantially the entire length of the lead assembly.

10. The lead assembly of claim 1 further comprising a non-conductive coating on each co-radially wound electrode wire.

11. The lead assembly of claim 10 wherein the non-conductive coating is a material selected from the group consisting of polyurethane, nylon, polyester, polyester-amide, polyester-imide, polyester-amide-imide, silicone, Teflon, expanded tetrafluoroethylene, polytetrafluoroethylene and combinations of the foregoing.

12. The lead assembly of claim 1 further comprising a non-conductive coating on one co-radially wound electrode wire.

13. The lead assembly of claim 12 wherein the non-conductive coating is a material selected from the group consisting of polyurethane, nylon, polyester, olyester-amide, polyester-imide, polyester-amide-imide, silicone, Teflon, expanded tetrafluoroethylene, polytetrafluoroethylene and combinations of the foregoing.

14. The lead assembly of claim 1 wherein each length of wire comprises a material selected from copper, titanium, titanium alloys, tungsten, gold and combinations of the foregoing.

15. The lead assembly of claim 1 wherein at least one of said co-radially wound electrode wires is a bondable wire.

16. The lead assembly of claim 15 wherein said bondable wire is heat, chemically or adhesively bondable.

17. The lead assembly of claim 1 further comprising an elongate flexible tubing constructed from a material selected from polyimide, polyolefin, expanded tetrafluoroethylene, polytetrafluoroethylene, polyetherketone and combinations of the foregoing wherein said co-radially wound wires are wound over said elongate tubing.

18. The lead assembly of claim 1 wherein said lead assembly is flexible.

19. The lead assembly of claim 1 wherein said lead assembly is rigid.

20. The lead assembly of claim 1 wherein the lead assembly is MRI compatible.

21. The lead assembly of claim 2 wherein said at least a first length of electrode wire is continuous and comprises a first plurality of discrete electrode wires; said at least a second length of electrode wire is continuous and comprises a second plurality of discrete electrode wires; and said at least a third electrode wire is continuous and comprises a third plurality of discrete electrode wires.

* * * * *